United States Patent [19]

Brooks et al.

[11] Patent Number: 4,496,555
[45] Date of Patent: Jan. 29, 1985

[54] COMPOUNDS AND COMPOSITIONS FOR INHIBITING ESTROGEN SULFOTRANSFERASE TRANSFERASE ACTIVITY, PROCESS AND NOVEL INTERMEDIATES THEREIN

[75] Inventors: Samuel C. Brooks, Orchard Lake; Jerome P. Horwitz, Oak Park, both of Mich.

[73] Assignee: Wayne State University, Detroit, Mich.

[21] Appl. No.: 515,335

[22] Filed: Jul. 19, 1983

[51] Int. Cl.³ .............................................. A61K 31/56
[52] U.S. Cl. ................................. 514/182; 260/397.4; 260/397.5; 260/397.3; 514/178; 514/177
[58] Field of Search ............................... 424/238, 243; 260/397.4, 397.5

[56] References Cited

U.S. PATENT DOCUMENTS 4,340,602  7/1982  Brooks .............................. 424/238

OTHER PUBLICATIONS

Rozhin et al., J. Biol. Chem., 1977, 252, 7214.
Musliner et al., "The Replacement of Phenolic Hydroxyl Groups by Hydrogen", J. Am. Chem. Soc. 88:18, pp. 4271–4273 (Sep. 20, 1966).
Morrow et al., "The Trienes", J. Med. Chem. 1966, vol. 9, pp. 249–251.
Yagupol'skii et al., "Aryl Trifluoromethanesulfoantes", Institute of Organic Chemistry, Academy of Sciences of the Ukranian SSR. Translation from Zhurnal Organicheskoi Khimii, vol. 7, No. 5, pp. 996–1001, May 1971.
L. R. Subramanian et al., "Perfluoroalkane Sulfonic Esters, Methods of Preparation and Applications in Organic Chemistry", Synthesis, 85–125 (1982).
J. Org. Chem., 1968, 33, pp. 2469–2473.
Tomson, A. J. and Horowitz, J. P. Org. Chem. 24, pp. 2056–2058 (1959).

*Primary Examiner*—Elbert L. Roberts
*Attorney, Agent, or Firm*—Joan Thierstein

[57] ABSTRACT

The present invention concerns the novel compounds having fluoro, amino, nitro or hydroxy monosubstituted at the 2- or 4- position on deoxyestrone as well as deoxyestra-17-ol. The compounds are useful as estrogen sulfotransferase inhibitors. Such estrogen sulfotransferase inhibition provides the novel use for treating a female mammal to prevent implantation of a blastocyst. Additionally, the invention concerns the novel synthesis and novel intermediates in the synthesis of the estrogen sulfotransferase inhibiting compound of the present invention.

26 Claims, No Drawings

COMPOUNDS AND COMPOSITIONS FOR INHIBITING ESTROGEN SULFOTRANSFERASE TRANSFERASE ACTIVITY, PROCESS AND NOVEL INTERMEDIATES THEREIN

The invention described herein was made in the course of work under a Public Health Service Grant from the Department of Health, Education and Welfare.

BACKGROUND OF THE INVENTION

This invention relates to novel compounds and compositions for use in terminating a pregnancy of a higher female primate having a defined menstrual or estrus cycle. The method of use is by administration to the pregnant female of a contragestative agent, which has estrogen sulfotransferase inhibitory activity and which prevents implantation of the blastocyst or fertilized egg. Further, the invention relates to novel processes having intermediates for synthesizing the novel compounds.

Compositions for use as estrogen sulfotransferase inhibitors are disclosed in U.S. Pat. No. 4,340,602. Such estrogen sulfotransferase inhibition provides highly effective contragestative agents for higher primates having a well defined menstrual or estrus cycle. Particularly such estrogen sulfotransferase agents are administered to a female patient who suspects that she is in the early stages of pregnancy. These agents are therefore effective for terminating pregnancies at a very early stage with minimal exposure of the patient to powerful steroidal medication. Additionally, unlike the widely used "pill", formulations which must be administered in anticipation of coitus, the compounds used in the method of the present invention are administered only when needed and then only for a relatively short time before or at the expected time of implantation.

It is shown by Rozhin et al, *J. Biol Chem.*, 1977, 252, 7214, that 4-nitroestrone 3-0-methylether blocks estrogen sulfurylation without interfering with the receptor binding and nuclear migration of physiological levels of $17\beta$-estradiol. However, Rozhin et al does not teach prevention of blastocyst implantation.

Further, the novel compounds of the present invention are not taught by the disclosure in either U.S. Pat. No. 4,340,602 or Rozhin et al.

The compounds within the scope of Formula T used as reactants to provide intermediates in the present invention are disclosed by Musliner et al, "The Replacement of Phenolic Hydroxyl Groups by Hydrogen", *J. Am. Chem. Soc.* 88:18, pp. 4271–3 (Sept. 20, 1966) for hydrogenolysis of various phenolic ethers. However, Musliner et al contains no teaching that would make obvious its use for the conversion of the substituted estrones within the present invention. Preparation of phenyl trifluoromethanesulfonate is shown by Yagupol'skii et al, "Aryl Trifluoromethanesulfoantes", Institute of Organic Chemistry, Academy of Sciences of the Ukranian SSR. Translated from *Zhurnal Organicheskoi Khimii* Vol. 7, No. 5, pp. 996–1001, May, 1971. Further, the hydrogenolysis of phenol or enols using perfluorosulfonates is shown by L. R. Subramanian et al, "Perfluoroalkane Sulfonic Esters, Methods of Preparation and Applications in Organic Chemistry", *Synthesis*, 85–125 (1982).

Replacement of an amino group at the 3-position of selected steroidal compounds by a fluoro is shown in Morrow et al, "The Trienes", *J. Med. Chem.* 1966, Vol. 9, pp. 249–51. Again, the teaching is limited so as to fail to teach the present invention.

As used in the specification and claims, "higher primate" includes those primate species in which the female generally has a predictable menstrual or estrus cycle. These species include the human, rhesus monkey, orangutang, chimpanzee, etc.

The method of the present invention may be used for other mammalian species including bovine and porcine animals.

Pregnancy is a condition of the female mammal in which a fertilized ovum is contained in her reproductive tract. For the purpose of this invention, the period of gestation or pregnancy is defined as beginning at the point of fertilization.

Nidation as used in the specification and claims, means the period of time in which the fertilized egg (blastocyst) attaches itself and penetrates within the epithelial lining of the uterus.

Implantation as used in the specification and claims means the period of time in which the blastocyst begins to form a placental membrane and to establish a direct connection with the blood supply of the mother. Although the exact process by which the active material is employed in the practice of this invention in terminating a pregnancy is unclear, it appears that the method of this invention interferes with the implantation process by decreasing the ability of the mother to support the life of the blastocyst. Thus, the gestation period is interrupted at a very early stage. Therefore, the method of this invention is to be considered as a method of preventing implantation or of contragestation, rather than as a method of abortion.

Particularly this invention relates to novel compounds for terminating a pregnancy comprising preventing implantation of a blastocyst in the epithelial uterine lining of a pregnant female by administration to the pregnant female during the period of implantation an amount of the compound effective to prevent implantation.

SUMMARY OF THE INVENTION

The present invention comprises:
(A) a compound of Formula I wherein $R_1$ is
  (a) a substituent having the formula $T_1$,
  (b) perfluoroalkylsulfonyl, or
  (c) hydrogen; and
  wherein $R_2$ and $R_3$ are the same or different and are
  (a) hydrogen,
  (b) hydroxy; or
  (c) taken together are keto; and
  with the proviso that both cannot be hydrogen at the same time; and wherein one of X is
  (a) halogen,
  (b) nitro,
  (c) amino, or
  (d) hydroxy; and
  with the proviso that the other X must always be hydrogen.
(B) A composition comprising a compound having the Formula XX wherein $R_2$ and $R_3$ are the same or different and are
  (a) hydrogen,
  (b) hydroxy, or
  (c) taken together are keto
  with the proviso that both cannot be hydrogen at the same time; and wherein one of X is
  (a) halogen, (b) nitro,
(c) amino, or
(d) hydroxy
with the proviso that the other X must always be hydrogen; and a pharmaceutically acceptable carrier.

(C) A method of treating a female mammal to prevent implantation of a blastocyst which method comprises administering an effective dosage of an estrogen sulfotransferase inhibiting compound selected from the group consisting of the Formula XX wherein $R_2$ and $R_3$ are the same or different and are
(a) hydrogen,
(b) hydroxy, or
(c) taken together are keto
with the proviso that both cannot be hydrogen at the same time; and wherein one of X is
(a) halogen,
(b) nitro,
(c) amino, or
(d) hydroxy
with the proviso that the other X must always be hydrogen.

(D) A process for the preparation of a compound having the Formula IV wherein $R_2$ and $R_3$ are different and are
(a) hydrogen, or
(c) hydroxy; and
wherein one of $X_1$ is
(a) halogen and
(b) the other $X_1$ must always be hydrogen;
which comprises
(a) reacting in an inert solvent a compound of Formula $I_1$
wherein one of $X_1$ is halogen and the other $X_1$ is hydrogen with a compound selected from the group consisting of Formula T or perfluoroalkylsulfonyl chloride of from one to four carbons; and
(b) reducing the product of (a) with a reducing agent, such as sodium borohydride and
(c) then hydrogenating in the presence of a catalyst to obtain Compound IV. See Schemes A and C denoted by the ( )'s.

(E) A process for the preparation of a compound having the Formula XI wherein $R_2$ and $R_3$ are different and
(a) hydrogen or
(b) hydroxy and
wherein one of $X_3$ is
(a) amino and the other $X_3$ is
(b) hydrogen
which comprises
(a) reacting in an inert solvent a compound having the formula $I_2$ wherein one of $X_2$ is
(b) nitro and the other $X_3$ is
(c) hydrogen with a perfluoroalkylsulfonyl chloride of from one to four carbons, inclusive; and
(b) reducing the product of (a) with a reducing agent such as sodium borohydride and
(c) then hydrogenating in the presence of a catalyst to obtain Compound XI
wherein one of $X_3$ is amino and the other $X_3$ is hydrogen. See Schemes B and C.

(F) A process for the preparation of a compound having the Formula IV/$V_1$ wherein $R_2$ and $R_3$ are
(a) hydrogen,
(b) hydroxy, or
(c) taken together are keto, and with the proviso that both cannot be hydrogen or hydroxy at the same time and wherein one of $X_1$ is
(a) halogen and the other $X_1$ is
(b) hydrogen
which comprises reacting in an inert solvent a compound of Formula XI
wherein one of $X_3$ is amino and the other is hydrogen and
wherein $R_2$ is hydroxy and $R_3$ is hydrogen with a halogenating agent. See Scheme D(1).

(G) A process for the preparation of a compound having the Formula XIII wherein one of $X_2$ is nitro and the other $X_2$ is hydrogen
which comprises reacting in an inert solvent a compound of Formula XI
wherein one of $X_3$ is amino and the other is hydrogen
wherein $R_2$ is hydroxy and $R_3$ is hydrogen with an oxidizing agent to obtain XIII. See Scheme D(2).

(H) A process for the preparation of a compound having the Formula XII wherein one of $X_4$ is hydroxy and the other $X_4$ is hydrogen which comprises reacting a compound having the formula XI
wherein one of $X_3$ is amino and the other is hydrogen and
wherein $R_2$ is hydroxy and $R_3$ is hydrogen with sodium nitrite in aqueous mineral acid to obtain XII. See Scheme D(3).

(I) A process for preparing a compound having the Formula V wherein one of X is
(a) halogen
(b) amino
(c) nitro
(d) hydroxy and the other X is
(e) hydrogen
which comprises reacting a compound having the formula IV/XI/XII/XIII wherein $R_2$ is hydroxy and $R_3$ is hydrogen and
wherein one of X is
(a) halogen
(b) amino
(c) nitro
(d) hydroxy and the other X is
(e) hydrogen with an oxidizing agent. See Scheme E.

The term "alkyl of from one to four carbon atoms, inclusive, is methyl, ethyl, propyl, butyl and isomers thereof.

"Halogen" is fluoro, chloro, bromo or iodo.

The term perfluoroalkyl includes an alkyl of from one to four carbons, inclusive; having all hydrogens substituted by fluoros. The preferred compound in this term is trifluoromethylsulfonyl chloride.

An intermediate VIII is formed in step (c) of the process described above in (E) when one of $X_2$ is nitro and $R_1$ is the Formula T. It may be isolated and treated further by hydrogenation as described in step (c). However, the hydrogenation of the intermediate VII formed by step (b) of the process described in (E) may be complete to yield some of the desired compound XI. The direct formation of XI from VII is shown by the broken → in Scheme b. In other words the catalytic reduction of 2- or 4- nitroestra-1,3,5(10)-trien-3,17-diol-3-0-(1-phenyl-1H-tetrazol-5-yl)ether VII to the desired 2- or 4-aminoestra-1,3,5(10)-trien-17β-ol XI is not as direct as the two step conversion of 2- or 4-nitroestrone to 2- or 4-nitroestra-1,3,5(10)-trien-3,17-diol 3-0-trifluoromethylsulfonate X followed by concurrent catalytic reduction of the nitro-substituent to an amino group and desulfonoxylation to the desired 2- or 4-aminoestra-1,3,5(10)-trien-17β-ol as shown in Scheme C.

This may then be followed by a Balz-Schiemann reaction to replace the amino group with a halogen substituent to give the desired compounds 2- or 4-haloestra-1,3,5(10)-trien-17-one. Such replacement is shown in Scheme D(1). Likewise, the 2- or 4- aminoestra-1,3,5(10)-trien-17β-ol may be the starting material to obtain 2- or 4- nitro or 2-or 4- hydroxy substituted estra-1,3,5(10)-trien-17β-ol as shown in Schemes D(2) and D(3), respectively.

Generally, in the Schemes one of $X_1$ is halogen and the other $X_1$ is hydrogen, one of $X_2$ is nitro and the other $X_2$ is hydrogen, one of $X_3$ is amino and the other $X_3$ is hydrogen, one of $X_4$ is hydroxy and the other $X_4$ is hydrogen. In Scheme C the $(X_1)$ indicate that the depicted reactions may be carried out when the substituents in the 2- or 4- position may be defined as $X_1$ above.

The $R_2$ and $R_3$ substituents herein may be defined in the form α-H:β-OH or α-OH:β-H wherein either H represents the substituent in the α configuration and OH in the β configuration or H represents the substituent in the β configuration and OH in the α configuration with respect to the plane of the ring to which the substituent is attached. However, the reduction of 2- or 4- substituted estrone 3-0-(1-phenyl-H-tetrazol-3-yl)ether; i.e. Formula I wherein $R_1$ is (1-phenyl-H-tetrazol-5-yl)oxy; one of X is halogen, nitro, amino or hydroxy, and the other one of X is hydrogen and $R_2$ and $R_3$ taken together are keto, to the corresponding 17-ol, wherein one of $R_2$ and $R_3$ is hydrogen and the other is hydroxy, with $NaBH_4$ occurs with high stereo selectivity (greater than 95:5) to the 17β-alcohol. This is defined when $R_2$ is hydroxy and $R_3$ is hydrogen. This reduction is shown in Scheme A, step b; Scheme B, step 2; and Scheme C, step y.

For convenience in assigning trivial names to compounds having the Formula I herein, when $R_2$ and $R_3$ taken together are keto the compounds shall be referred to as estrone. Further, when compounds having the Formula I herein when $R_2$ and $R_3$ are both hydroxy; the chemical skeleton described shall be referred to as 17β- and 17α- estradiol.

The compounds within the scope of the invention are useful either as agents for treating a female mammal to prevent implantation of a blastocyst by inhibiting estrogen sulfotransferase production or as intermediates in processes for synthesizing the agents (hereinafter referred to as estrogen sulfotransferase inhibiting agents).

The compounds within the scope of the present invention which are the estrogen sulfotransferase inhibiting agents are the compounds of Formula I wherein $R_1$ is hydrogen and one of $R_2$ and $R_3$ is OH and the other is H, or $R_2$ and $R_3$ taken together are keto.

The compounds within the scope of the present invention which are useful as intermediates in synthetic processes to make the sulfontransferase inhibiting agents of the invention are those of Formula I wherein $R_1$ is (a) $T_1$ wherein $R_4$ is alkyl of from one to four, inclusive; or phenyl; or (b) perfluoroalkylsulfonyl. In these intermediates one of $R_2$ and $R_3$ may be hydroxy and the other is hydrogen or $R_2$ and $R_3$ may be taken together as keto. Also intermediates are compounds of the invention having the Formula I wherein $R_1$ is hydrogen and $R_2$ and $R_3$ are the same or different and are hydrogen or hydroxy with the proviso that both cannot be hydrogen at the same time. These later intermediates may be treated to obtain the estrogen sulfotransferase inhibiting agents of Formula I wherein $R_2$ and $R_3$ taken together are keto.

The compounds within the scope of the invention which are useful for treating a female mammal to prevent implantation of a blastocyst are sulfotransferase inhibiting agents. Preferred compounds of the invention are those wherein one of X is fluoro and the other is hydrogen. With respect to the $R_2$ and $R_3$ substituents those compounds wherein $R_2$ is hydroxy and $R_3$ is hydrogen or $R_2$ and $R_3$ when taken together are keto, are preferred. Most preferred are the compounds wherein one of X is fluoro and $R_2$ and $R_3$ are hydroxyl and hydrogen, respectively. On the other hand, while the estrogen sulfotransferase inhibiting potency of the sulfotransferase inhibiting agents within the scope of the invention will vary against the implantation or for contragestation in a particular environment, each estrogen sulfotransferase inhibiting agent within the scope of the invention will be useful against implantation or as a contragestation agent in at least one environement in which inhibition is desirable.

The estrogen sulfotransferase inhibiting agents within the scope of the invention are useful to prevent implantation of a blastocyst in a female mammal, including humans. A detailed description of the determination of inhibition of estrogen sulfotransferase is found in U.S. Pat. No. 4,340,602 which is incorporated herein by reference. To be effective as an estrogen sulfotransferase inhibiting agent in an environment, the sulfotransferase inhibiting compounds within the scope of this invention must be introduced into the environment, by one of several means which are well known in the art, and which are described in more detail below, in a quantity sufficient to inhibit implantation of the fertilized ovum "blastocyst" within the epithelial lining of the uterus.

DETAILED DESCRIPTION OF THE INVENTION

The novel compounds useful herein are prepared by conversion of known 2- or 4- substituted estrone. The estrone is illustrated, with numbering of carbon positions, in Formula Iq, wherein one of Q is halogen or nitro and the other Q is hydrogen.

The novel compounds having use as estrogen sulfotransferase inhibiting activity are 2- or 4-substituted 3-deoxy estrone V or 2- or 4-substituted estra-1,3,5(10)-triene-17β-ol having Formulae IV, XI, XII or XIII.

The illustrative examples below and the following Tables I and II describe the preparation and use of novel compounds and processes herein. Variations from the details given herein, e.g. solvent, temperature or other reaction conditions, provided in the discussion and examples are also contemplated as part of the invention. The discussion and examples are intended, therefore, to be illustrative, not comprehensive. Except as otherwise noted, however, the examples do set forth preferred conditions for the reactions exemplified.

Compounds of Formula $I_1$ wherein one of $X_1$ is halogen and the other $X_1$ is hydrogen and Formula $I_2$ is nitro and the other is hydrogen are the starting materials for synthesizing all compounds within the scope of this invention. All compounds of $I_1$ and $I_2$ are known. For the 4-fluoroestrone within the definition of Formula $I_1$ see Utne et al, *J. Org. Chem.*, 1968, 33, pp. 2469–2473. The 4-nitroestrone having the Formula $I_2$ is found in Tomson, A. J. and Horowitz, J. P., *J. Org. Chem.*, 24 pp. 2056–2058 (1959).

Generally, the process for preparing 2- or 4-substituted estrones having either the substituent $T_1$ or trifluoromethylsulfonyl at the 3-position is described above in (D) step (a) and (E) step (a). Specifically, the step (a) in Scheme A; step (1) in Scheme B; and step (x) in Scheme C show the reactions. Such reactions are performed in any organic solvent which is inert with the reactants and in which the reactants are soluble. For example, dry acetone, N, N-dimethylformamide, or dichloromethane, preferably acetone. The reaction mixture is refluxed for from 4 to 24 hrs, preferably 12 to 24 hrs.

The reduction of compound having Formula II, VI, and IX in Scheme A step (b), Scheme B step (2) and Scheme C step (y), respectively, are carried out in any organic solvent in which the reactants are soluble. Such solvents include, for example, acetic acid, dimethyl ether, diethyl ether, tetrahydrofuran, methanol, or toluene containing hexadecyltributylphosphonium bromide. The preferred solvent is aqueous methanol. Sodium borohydride ($NaBH_4$) is added to the solution. Generally, temperatures between 0° C. and 60° C. are acceptable. Preferred temperatures are 20° to 30° C.

Further reduction of intermediates shown as compound III in Scheme A, compound VII in Scheme B and compound X of Scheme C are accomplished under hydrogen pressure in the presence of a catalyst; for example, palladium on carbon. This hydrogenation removes the 3-0 ether at the 3- position; except for the production of compound VII discussed above, to yield the desired deoxyestrone having the formula IV, XI and IX. Additionally, if the substituent X is the nitro group as shown in Scheme B and Scheme C, the resulting product is a converted nitro such that an amino is substituted at the 2- or 4- position on a deoxyestra-1,3,5(10)-trien-17β-ol.

Compounds having IV, XI, XII and XIII as shown in Scheme E can be oxidized to deoxyestrone by treatment with an oxidizing agent; such as chromium trioxide in inert organic solvents such as, for example, acetone, or pridine, in the presence of ammonium sulfate. The treatment is performed at a temperature of from 20° C. to 35° C.

Finally, estra-1,3,5(10)-trien-17β-ol substituted by amino in the 2- or 4- position; in this instance compounds of Formula XI in Scheme D, are treated with appropriate reagents to prepare halogen, nitro or hydroxy groups in the 2- or 4- positions of estra-1,3,5(10)-trien-17β-ol.

Conventional separation methods are used for any of the above described processes.

The compounds of Formula IV, XII and XIII are useful either as intermediates in processes to synthesize estrogen sulfotransferase inhibiting agents or as estrogen sulfotransferase inhibiting agents. Likewise, compounds of Formula XI are also useful as intermediates in processes to synthesize compounds within the scope of the present invention which are estrogen sulfotransferase inhibiting agents or as estrogen sulfotransferase inhibiting agents themselves.

The estrogen sulfotransferase inhibiting activity of compounds within the scope of the invention are determined by inhibition of bovine adrenal or porcine uterine estrogen sulfotransferase. The desired concentration of estrogen sulfates is determined by comparisons after appropriate incubations with and without inhibitors and at various concentrations of inhibitors in the incubation. A detailed description of materials and methods for both bovine adrenal sulfotransferase inhibition and metabolism of estrogen in porcine uterus during implantation is described in U.S. Pat. No. 4,340,602 incorporated herein by reference above. Additionally, U.S. Pat. No. 4,340,602 describes materials and methods for determining estrogen sulfurylation in human endometrial curettings.

It is now believed that the 3-alkyl ethers of U.S. Pat. No. 4,340,602 are dealkylated by the liver resulting in a 3-hydroxy compound capable of binding to a receptor in the same manner as previously known for estrogen-like compounds. Such dealkylation and resulting receptor binding is undesirable for selected forms of administration, particularly oral. The present invention avoids any possible metabolism of this kind since all the compounds herein are 3-deoxy compounds.

Based on results with the technique applied to the control, a compound is judged active for preventing implantation of the fertilized ovum during nidation by the level of estrogen sulfotransferase inhibition in each case. By this criterion, all the estrogen sulfotransferase inhibiting compounds within the scope of the invention are active. The demonstration of the activity can be found in the following charts.

TABLE I

| Purufied Bovine Adrenal Estrogen Sulfotransferase Inhibition with 4-Fluoro-1,3,5(10)estratriene 17β-ol | | |
|---|---|---|
| Compound | % Inhibition* | $K_i$ |
| 4-F-1,3,5(10)estratriene 17β-ol | 81 | 6 |

*Methods described in: Rozhin, J., et al. J. Biol. Chem. 252, 7214 (1977).

TABLE II

| Inhibition of Porcine Uterine Estrogen Sulfotransferase by 4-F-1,3,5(10)estratriene-17β-ol | |
|---|---|
| Incubation$^a$ | Estrogen Sulfates$^c$ p mole |
| Control +4-F-Estratriene-17β-ol$^b$ | 1.26 |
| 10-fold | 1.07 |
| $10^2 \lambda$-fold | 1.08 |
| $10^3 \lambda$-fold | 0.67 |

Minimum inhibitory concentrations are an effective antiimplanation amount. Generally the amount of a single daily dose required to produce such an effect is a dosage of from 0.1–500 ml of active ingredient. Dosage forms may be administered one or more times per day for one day or preferably for several days during the period of administration. The active inhibitor of estrogen sulfotransferase of this invention may be administered orally, intrauterinally, intravaginally or parentally. The dosage depends on factors such as the method of administration, the scheduling of dosages and the weight and age of the particular primate being treated.

In the practice of this invention the active compounds are administered during the period of implantation immediately prior to the period of nidation. In higher female primates, which have a 26–32 day menstrual cycle, the nidation period is about days 18–23 of the menstrual cycle, counting the onset of the previous menstration as the first day of the menstrual cycle. The period of implantation is considered as beginning during the 21st day of the same cycle. Within fourteen days, placental circulation is usually considered to be complete. In the human female, nidation commonly occurs on or about the 20th day of the cycle. Implantation generally occurs a day later, about the 21st day, of the same cycle. By about the 35th day, placental circulation is considered to be completed. Accordingly, the compounds of the present invention are administered on about 21 days after the onset of menstrual bleeding. Administration can be continued daily for 3–9 days 21–35 of the particular menstrual cycle. Preferably the active compounds are administered for 6–8 days. Administration of the active compounds must be during the effective period but need not be limited to this time.

Compounds used in the practice of the invention can be administered in various unit dosage forms and may be taken orally in the form of lozenges or troches containing an inert diluent or other physiologically acceptable edible carrier. If intravaginal administration is selected, local absorption by the vaginal or cervical mucosa will take place. Preparation for this purpose include vaginal creams, jellies and ointments. Topical ointments containing the active ingredient in an ointment base such as petrolatum, lanolin, polyethylene glycol or mixtures thereof are typical of those used for this mode of administration. Generally, the active steroidal sulfotransferase inhibitor is finely divided by milling or grinding and then admixed with the carrier.

Creams and lotions are also acceptable for intravaginal administration. These are prepared by dispensing the active ingredient in an oily phase and forming an emulsion therefrom. A formulation which is preferred for vaginal administration is a stable, non-aqueous, areosal foam which readily collapses at body temperatures and spreads as a uniform film along the vaginal walls. These compositions are considered to be cosmetically superior to other formulations because they do not produce a sensation of warmth or dehydration when applied. Also, the are neither greasy nor tacky and will not stain clothing. Soft cushiony foams can be prepared and administered intravaginally.

The medicaments used in the practice of this invention can also be administered in a medicated tampon containing the active ingredient. The tampon is applied on or about the expected date of The menstrual period. The active ingredient is released at an acceptable predetermined rate.

If a fertilization had occurred, release of the active ingredient and its subsequent absorption serves to prevent implantation of the blastocyst with resulting contragestation and production of a normal menstrual period.

An effective quantity of the compound is employed in treatment. The dosage of the compound for treatment depends on many factors that are well known to those skilled in the art. They include, for example, the route of administration and the potency of the particular compound. A dosage schedule for humans of from about 2 to about 4,000 ml of compound in a single dose administered parentally or in composition of this invention are effective for estrogen sulfotransferase inhibition. More specifically, a single dose is from 5 ml to about 1,000 ml in a single dose. More specifically, the dose is from 10 ml to about 500 ml of compound.

EXAMPLES

The following examples are indicative of the scope of this invention and are not to be construed to be limitative. Those skilled in the art will recognize appropriate variations from the processes, both as to the precursors as well as reaction conditions and techniques.

The operation of the present invention is particularly illustrated by the examples below.

EXAMPLE 1

4-Fluoroestrone 3-O-(1-Phenyl-1H-tetrazol-5-yl) Ether (II). See Scheme A step (a).

A solution of 4-fluoroestrone (I, 210 mg, 0.73 mmol), prepared according to the method of Utne et al, cited above, and 5-chloro-1-phenyl-1-H-tetrazole (130 mg, 0.73 mmole) in 30 of anhydrous acetone containing anhydrous potassium carbonate (210 mg, 1.46 mmole) and protected from moisture is refluxed for 24 hr. The reaction mixture is filtered through a pad of Celite and the filtrate is evaporated to dryness. The residue is dissolved in dichloromethane and the solution is washed first with ($2 \times 5$ ml) 10% NaOH and then with water. The solution is dried over sodium sulfate and evaporated to dryness. The residue is crystallized from absolute ethanol in the form of fine, colorless needles of 4-fluoroestrone 3-O-(1-phenyl-1H-tetrazol-5-yl)ether II (250 mg, 79% yield): mp 161°–163° C; $^1$H NMR $\delta$ 7.89–7.54 (m, 5, $C_6H_5$) 7.39, 7.19 (dd, 2, aromatic $H_1$, $H_2$), 2.92–1.45 (m, 15) 0.93 (s, 3, $C_{18}$ $CH_3$); I (KBr) 1720 cm$^{-1}$ ($C_{17}$ C=O). Anal. Calc'd. for $C_{25}H_{25}FN_4O_2$: C, 69.42; H, 5.83, N, 12.96 F, 4.39. Found: C, 69.36; H 5.83; N 12.78; F, 4.51.

EXAMPLE 2

4-Fluoroestra-1,3,5-(10)-trien-17$\beta$-ol (IV)

(a) To a solution of 4-fluoroestrone 3-O-(1-phenyl-1H-tetrazol-5-yl)ether as prepared in Example I (II, 220 mg, 0.5 mmol) in methanol (75 ml) is added, at room temperature with stirring, a solution of sodium borohydride (120 mg, 1.5 mmol) in 2 ml of 25% aqueous methanol and the mixture is stirred for 45 min. The solvents are evaporated at reduced pressure and the residue, dissolved in 10 ml dichloromethane, is washed with dilute (2%) HCL. The solution is dried ($Na_2SO_4$) and after evaporation to dryness yields a colorless foam 4-fluoroestra-1,3,5(10)-trien-17-diol-3-O-(1-phenyl)-1H-tetrazole-5-yl) ether III (260 mg, 74% yield) which appears as a single spot on TLC ($S_3$) and whose infrared spectrum is characterized by the disapperance of 17-keto absorption. See Scheme A step (b).

(b) Unrecrystallized III as prepared in (a) (160 mg, 0.37 mmol), is dissolved in 50 ml of EtOH containing 40 mg (25% by wt.) of 10% Pd/C, hydrogenolyzed for 18 hr. in a Parr apparatus pressurized to 53 psi. The solution is filtered with Celite and evaporated to dryness. The residue is dissolved in dichloromethane which is washed first with ($2 \times 10$ ml) 10% NaOH and then with water. The solution is dried over sodium sulfate to reveal the presence of three products on TLC ($S_3$). The slowest moving material is separated on preparative TLC with the same solvent system which, on evaporation, gives 4-fluoroestra-1,3,5(10)-trien-17$\beta$-ol IV as a foam, wt. 50 mg, 49% yield. $^1$H NMR 7.15–6.79 (m, 3, aromatic), 3.73 (t, 1, $H_{17}\alpha$), 2.84–1.26 (m, 16) 0.78 (s, 3, $C_{18}CH_3$); mass spectrum: m/z 275 (M$^+$ +1). Anal. Calc'd. for $C_{18}H_{23}FO$: C, 78.79, H, 8.45; F. 6.92. Found: C, 78.61; H, 8.85; F, 7.06. See Scheme A step (c).

EXAMPLE 3

4-Fluoroestra-1,3,5-(10)-trien-17-one (V). See Scheme E.

To a solution of 4-fluoroestra-1,3,5-(10)-trien-17$\beta$-ol IV as prepared in Example 2 (100 mg, 0.36 mmol) in 1.5 ml of acetone at 0° C. is added, dropwise with stirring, a solution of (95ml) of 8N chromium trioxide in ammonium sulfate. After approximately 5 min. the reaction mixture is poured into 75 ml of ice-water and the solids are collected. The filter cake is stirred with methanol, the inorganic salts are removed and the filtrate is evaporated to dryness to give the crude product, 4-fluoroestra-1,3,5-(10)-trien-17-one as a tan solid. The latter crystallizes from ether-petroleum ether (30°-60°) as a colorless solid (60 mg, 61% yield), mp 139°-141° C. Ir (KBr)cm$^{-1}$ 1724 ($C_{17}$ C=O), 1230 (aryl fluoride); $^1$H NMR $\delta$7.21-6.81 (m, 3, $H_1$, $H_2$, $H_3$ aromatic) 2.91-1.54 (m, 15), 0.92 (s, 3, $C_{18}CH_3$). Anal. Calc'd. for C, 79.38; H, 7.77; F, 6.98. Found: C, 79.53; H, 7.76; F, 7.13.

EXAMPLE 4

4-Nitroestrone 3-O-(1-Phenyl-1H-tetrazol-5-yl) Ether (VI). See Scheme B step (1).

A solution of 4-nitroestrone (1.26 g, 4 mmol) in 50 ml of dry acetone, containing anhydrous potassium carbonate (1.12 g, 8 mmol) and 5-chloro-1-phenyl-1H-tetrazole (720 mg, 4 mmol), is refluxed for 24 hr. The cooled reaction mixture is filtered through Celite and the filtrate is evaporated to dryness under reduced pressure. The residue is dissolved in 100 ml of dichloromethane, which is then washed twice with (10ml) 10% sodium hydroxide solution and the solution is dried over sodium sulfate. The filtered solution is evaporated to dryness and the product, 4-nitroestrone-3-O-(1-phenyl 1H-tetrazol-5-yl)ether (VI) crystallized from absolute ethanol in the form of yellow needles, wt. 1.36 g, 74% yield, mp. 169°-171° C. Ir(KBr) cm $^{-1}$ 1720 ($C_{17}$ C=O); $^1$H NMR 7.70-7.50 (m, 7, aromatic), 2.86-1.22 (m, 15), 0.92 (s, 3, $C_{18}CH_3$). Anal. Calc'd. for $C_{25}H_{25}N_5O_4$; H, 5.48; N, 15.24. Found: C, 65.47; H, 5.51; N, 15.21.

EXAMPLE 5

4-Nitroestra-1,3,5(10)-trien-3,17-diol 3-O-(1-Phenyl-1H-tetrazol-3-yl) Ether (VII). See Scheme B step (2).

The reduction of 4-nitroestrone-3-O-(1-phenyl-1H-tetrazole-5-yl)ether VI as prepared in Example 4 (920 mg, 2 mmol) in aqueous methanol with sodium borohydride (230 mg, 6 mmol) is carried out as described above in Example 2 to obtain 4-nitroestra-1,3,5(10)-trien-16-diol-3-O-(1-phenyl-1H-tetrazol-3-yl)ether VII a colorless foam (7, 700 mg, 76% yield) which is employed directly in the subsequent reduction $^1$H NMR $\delta$7.72-7.50 (m, 7, aromatic), 2.89-1.28 (m, 16), 0.79 (s, 3, $C_{18}CH_3$). Ir(KBr) showed the disappearance of $C_{17}$ C=O).

EXAMPLE 6

4-Aminoestra-1,3,5(10)-trien-17δ-ol XI. See Scheme B step (3).

A solution of 4-nitroestra-1,3,5(10)-trien-17-diol 3-O-(1-phenyl-1-H-tetrazol-3-yl)ether VII as prepared in Example 5 (460 mg, 1 mmol) in 75 ml of ethanol is hydrogenated at 53 psi of hydrogen pressure (Parr shaker) over 90 mg (20% by wt.) of 10% Pd/C catalyst for 17 hr. The reaction mixture is filtered through Celite and the filtrate is evaporated to dryness. The residue is suspended in dichloromethane (25 ml) and the mixture is washed twice, first with (5ml) 10% sodium hydroxide, then with water and dried over anhydrous sodium sulfate. The filtered solution is evaporated to an oil which solidifies on trituration with ether. The solid is recrystallized from methanol to give 140 mg (32% yield) of 4-aminoestra-1,3,5(10)-trien-17-β-ol 3-O-(1-phenyl-1-H-tetrazol-3-yl)ether (VIII), mp 217°-219° C. $^1$H NMR $\delta$7.84-7.52 (m, 5, aromatic) 7.14, 7.80 (dd, 2, $H_1$, $H_2$), 3.72-3.42 (t, 1, $H_{17}$), 2.52-1.13 (m, 18), 0.77 (s, 3, $C_{18}CH_3$). Anal. Calc'd. for $C_{25}H_{29}N_5O_2$; 69.58; H, 6,77; N, 16.23. Found: C, 69.71; H, 6.96; N, 16.39.

EXAMPLE 7

4-Fluoroestra-1,3,5(10)-trien-17-one V. See Scheme D (1).

(b) A solution of (230 mg, 0.85 mmol) 4-aminoestra-1,3,5(10)-trien-17β-ol (XI) a prepared in Example 6 in 4.6 ml of ethanol containing 2.3 ml of 48% hydrofluoroboric acid, is cooled to 0° C. and maintained at this temperature with stirring during dorpwise addition of an aqueous solution (230 ml) of sodium nitrite (60 mg, 0.88 mmol). After 1 hr. of stirring at 0°, the reaction mixture is first treated with a few crystals of urea and then poured into 150 ml of ether. The product, a colorless solid, is collected and dried at room temperature in vacuo over $P_2O_5$ for 24 hr., wt. 220 mg (70% yield).

The diazonium fluoborate derivative (160 mg, 0.59 mmol) is suspended in 25 ml of a mixture of dry xylenes and refluxed for 3 hr. The cooled suspension is filtered and the filtrate, which showed on TLC ($S_1$), the presence of three products, including 4-fluorestra-1,3,5-(10)-trien-17-ol, is evaporated to dryness. The residue was subjected to preparative TLC ($S_1$) and the desired product, 4-fluoestra-1,3,5-(10)-trien-17-one (V) was isolated as a foam (wt. 60 mg, 37% yield). The latter, on (mass and $^1$H NMR) spectral analyses, proves to be identical in all respects with a sample of V obtained from Example 3.

EXAMPLE 8

4-Nitroestrone 3-O-(trifluoromethyl)sulfonate (IX). See Scheme C step (x).

To a solution of 4-nitroestrone ($I_2$ 630 mg, 2 mmol) in 50 ml dry acetone containing 350 ml (2.5 mmol) of triethylamine is added 265 ml (2.5 mmol) of trifluoromethanesulfonyl chloride and the reaction mixture, protected from moisture, is refluxed for 3 hr. The solvent is evaporated to dryness and residue is dissolved in 100 ml of dichloromethane. The solution is washed and dried over sodium sulfate. The filtered solution is evaporated to dryness and the residue, 4-nitroestrone-3-O-(trifluoromethyl)sulfonate (IX), which shows a single spot on TLC ($S_2$), crystallizes from 2-propanol in the form of yellow needles, wt. 700 mg, (78% yield), mp 198°-202° C. Ir (KBr) cm$^{-1}$ 1740 ($C_{17}$ C=O), 1545, 1370 ($NO_2$), 1430, 1220 (—$OSO_2$—). $^1$H NMR 7.53, 7.28 (dd, 2, aromatic $H_1$, $H_2$), 3.00-1.2 (m, 15), 0.93 (s, 3, $C_{18}CH_3$). Anal. Calc'd. for $C_{19}H_{20}NO_6SF_3$: C, 51.00; H, 4.51; N, 3.13; S, 7.17; F, 12.74. Found: C, 51.13; H, 4.66; N, 3.03; S, 6.93; F, 12.56.

EXAMPLE 9

4-Nitroestra-1,3,5(10)-triene-3,17-diol 3-O-(Trifluoromethyl)-Sulfonate (X). See Scheme C step (y).

To a solution of 230 mg (0.5 mmol) of 4-nitroestrone 3-0-(trifluoromethyl)sulfonate (IX) as prepared in Example 8 in 230 ml of toluene, containing hexadecyltributylphosphonium bromide (26 mg, 0.05 mmol) is slowly added a solution of sodium borohydride (60 mg 1.5 mmol) in 150 ml of water and the mixture is stirred at room temperature for 3 hr. Additional (10 ml) toluene is added and the organic layer is separated, then washed with water. The toluene solution is dried over sodium sulfate and then evaporated to an oily residue, which gives a colorless foam of 4-nitroestra-17-diol 3-0-(trifluoromethyl)-sulfonate (X) (184 mg, 82% yield) on evaporation from ether. Ir (KBr) cm$^{-1}$ 1540, 1365 (NO$_2$), 1430, 1230 (—OSO$_2$—). $^1$H NMR δ7.52, 7.26, (dd, 2, aromatic H$_1$, H$_2$), 3.68 (t, 1.17 H), 2.88-1.28 (m 16), 0.80 (s, 3, C$_{18}$CH$_3$). Anal. Calc'd. for C$_{19}$H$_{22}$NO$_6$SF$_3$: C, 50.77; H, 4.93; N, 3.12; S, 7.14; F, 12.68. Found: C, 50.58; H, 5.03; N, 3.00; S, 6.95; F, 12.79.

EXAMPLE 10

4-Aminoestra-1,3,5(10)-trien-17β-ol (XI) (a). See Scheme C step (z).

A solution of X (2.13 g, 4.74 mmol) as prepared in Example 9 in 100 ml of methanol containing triethylamine (6.60 L, 4.8 mmol) and 10% Pd/C (430 mg, 20% by weight) is hydrogenated in a Parr apparatus at 16 psi for 5 hr. TLC (S$_3$) shows one major product and 3 minor constituents. The reaction mixture is filtered through Celite and the filtrate is evaporated to dryness. The residue is dissolved in excess dichloromethane and the solution is washed with water. The extract is dried over sodium sulfate and filtered. The filtrate is evaporated to dryness. The residue crystallizes from methanol as a cluster of colorless needles of 4-aminoestra-1,3,5(10)-trien-17β-ol (XI) wt. 320 mg. (25% yield), mp. 189°-192° C. Mass Spectrum: m/z 271 (M+), 237 (M-(H$_2$O+NH$_2$). $^1$H NMR 7.23-6.51 (m, 3, H$_1$, H$_2$, H$_3$ aromatic) 3.71-3.45 (t, 1, 17 H), 2,57-1.23 (m, 18), 0.76 (s, 3, C$_{18}$CH$_3$). Anal. Calc'd. for C$_{18}$H$_{25}$NO: C, 79.66; H, 9.28; N, 5.16. Found: C, 79.72; H, 9.11; N, 4.97.

Formulae

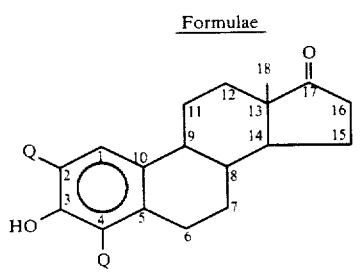

Iq

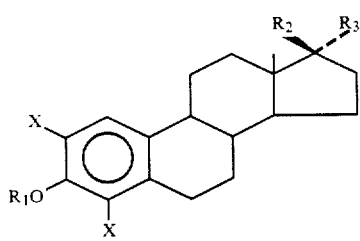

I

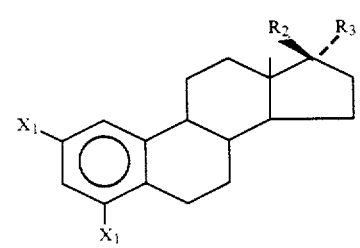

IV/V$_1$

-continued
Formulae

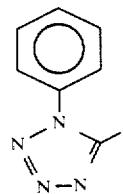

T$_1$

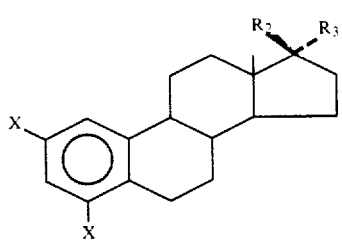

XX

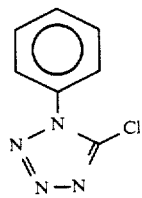

T

Scheme A

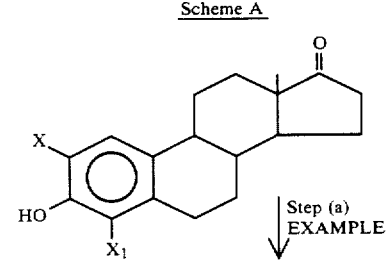

I$_1$

Step (a)
EXAMPLE

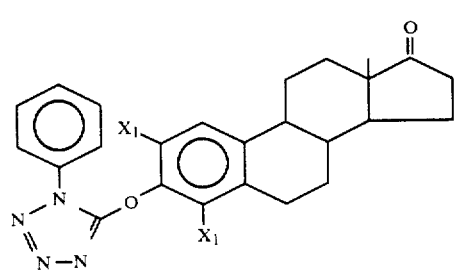

II

Step (b)
EXAMPLE 2a

-continued
Scheme A
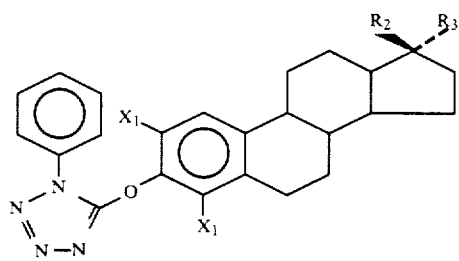
III
Step (c)
EXAMPLE 2b
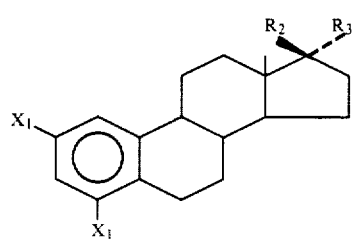
IV
Scheme B
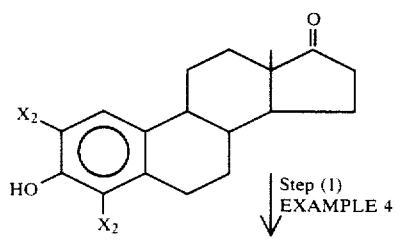
$I_2$
Step (1)
EXAMPLE 4
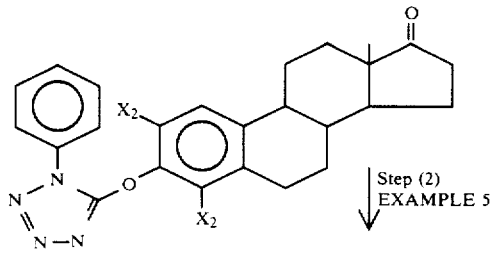
VI
Step (2)
EXAMPLE 5
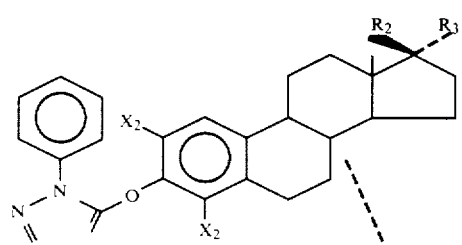
VII
Step (3a) EXAMPLE 6
Step (3) EXAMPLE 6
-continued
Scheme B
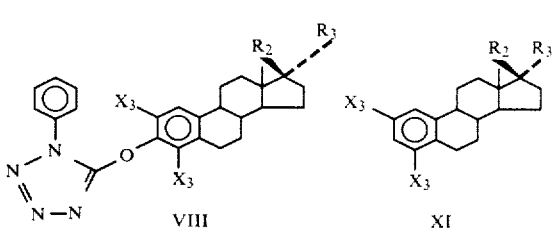
VIII     XI
Scheme C
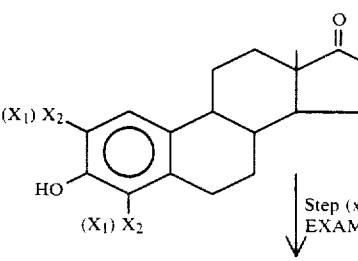
$(I_1) I_2$
Step (x)
EXAMPLE 9
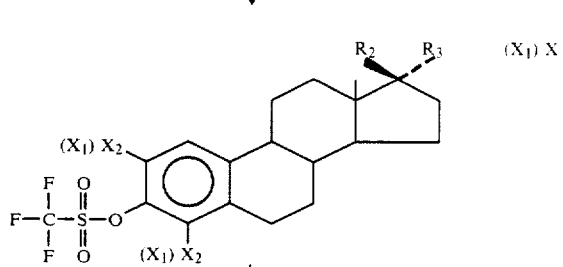
$(IX_1) IX$
Step (y)
EXAMPLE 10
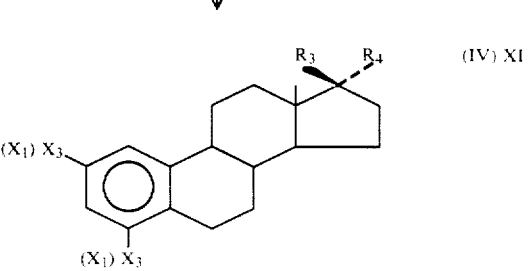
$(X_1) X$
Step (z)
EXAMPLE 10
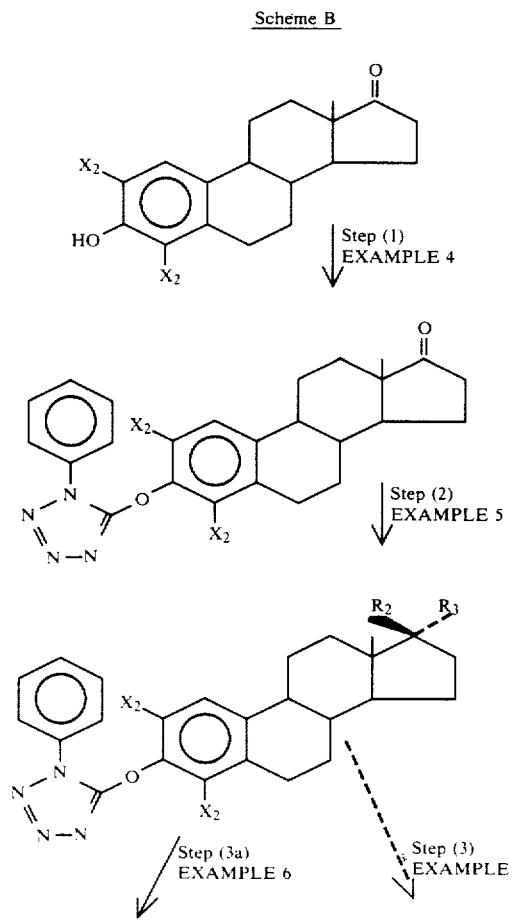
$(IV) XI$

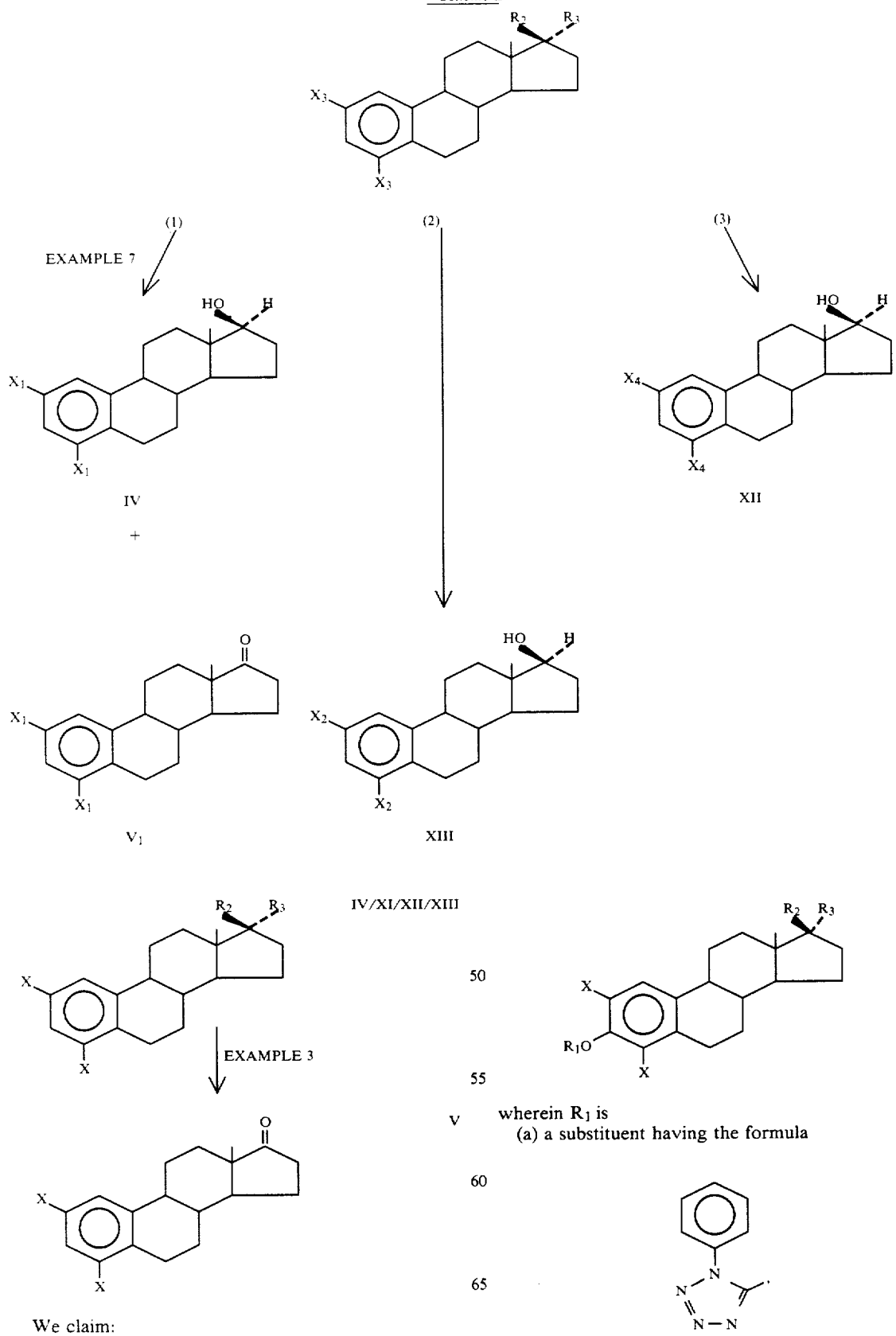
We claim:
1. A compound having the formula
wherein $R_1$ is
(a) a substituent having the formula
$T_1$, (b) perfluoroalkylsulfonyl of from 1–4 carbon atoms, inclusive;

and wherein $R_2$ and $R_3$ are the same or different and are
 (a) hydrogen,
 (b) hydroxy; or
 (c) taken together are keto; and
with the proviso that both cannot be hydrogen at the same time; and wherein one of X is
 (a) halogen,
 (b) nitro,
 (c) amino, or
 (d) hydroxy; and
with the proviso that the other X must always be hydrogen.

2. A compound of claim 1 wherein $R^1$ is trifluoromethylsulfonyl.

3. A compound of claim 1 wherein $R_2$ and $R_3$ taken together are keto or $R_2$ is hydroxy and $R_3$ is hydrogen.

4. A compound of claim 3 wherein one of X is halogen, nitro or amino.

5. A compound of claim 1 wherein X is fluoro.

6. A compound of claim 4 wherein the specific embodiment is 4-fluoroestra-1,3,5(10)-trien-17β-ol.

7. A compound of claim 3 wherein X is amino so the specific embodiment is 4-aminoestra-1,3,5(10)-trien-17β-ol.

8. A compound of claim 2 selected from the group cosisting of 4-fluoroestrone 3-0-(1-phenyl-1H-tetrazol-5-yl)ether, 4-nitroestrone 3-0-(1-phenyl-1-H-tetrazol-5-yl)ether, 4-aminoestra-1,3,5(10)-trien-3,17β-diol 3-0-(1-phenyl-1-H-tetrazol-3-yl)ether, 4-nitroestrone 3-0-(trifluoromethyl)sulfate, 4-nitroestra-diol 3,17β-diol 3-0-(trifluoro-methyl)sulfate.

9. A composition comprising a compound having the formula

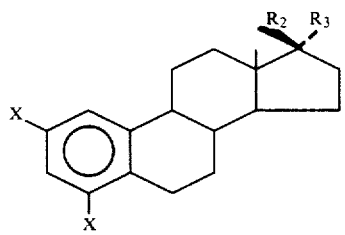

XX wherein $R_2$ and $R_3$ are the same or different and are
 (a) hydrogen,
 (b) hydroxy, or
 (c) taken together are keto
with the proviso that both cannot be hydrogen at the same time; and wherein one of X is
 (a) halogen,
 (b) nitro,
 (c) amino, or
 (d) hydroxy
with the proviso that the other X must always be hydrogen; and a pharmaceutically acceptable carrier.

10. A composition of claim 8 wherein $R_2$ and $R_3$ taken together are keto or $R_2$ is hydroxy and $R_3$ is hydrogen.

11. A composition of claim 9 wherein one of X is halogen, nitro or amino.

12. A composition of claim 10 wherein X is fluoro.

13. A composition of claim 8 wherein the compound is 4-fluoroestra-1,3,5(10)trien-17β-ol.

14. A composition of claim 9 wherein X is amino so the preferred embodiment is a compound consisting of 4-aminoestra-1,3,5(10)-trien-17β-ol.

15. A method of treating a female mammal to prevent implantation of a blastocyst which method comprises administering an effective dose of an estrogen sulfotransferase inhibiting compound selected from the group consisting of the formula

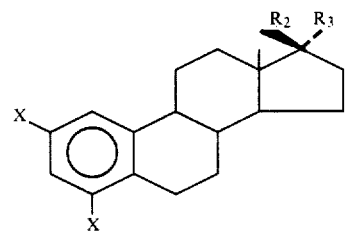

XX wherein $R_2$ and $R_3$ are the same or different and are
 (a) hydrogen,
 (b) hydroxy, or
 (c) taken together are keto
with the proviso that both cannot be hydrogen at the same time; and wherein one of X is
 (a) halogen,
 (b) nitro,
 (c) amino, or
 (d) hydroxy and with the proviso that the other X must always be hydrogen; and a pharmaceutically acceptable carrier.

16. A method of claim 14 wherein $R_2$ and $R_3$ taken together are keto or $R_2$ is hydroxy and $R_3$ is hydrogen.

17. A method of claim 16 wherein X is hydrogen, halogen, nitro or amino.

18. A method of claim 17 wherein X is fluoro.

19. A method of claim 17 wherein the compound is 4-fluoroestra-1,3,5(10)trien-17β-ol or 4-aminoestra-1,3,5(10)-trien-17β-ol.

20. A process for the preparation of a compound having the formula

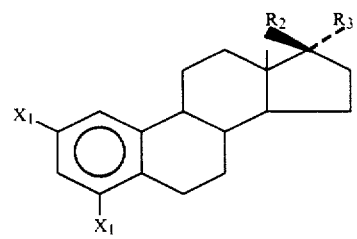

IV wherein $R_2$ and $R_3$ are different and are
 (a) hydrogen, or
 (b) hydroxy; and
wherein one of $X_1$ is
 (a) fluorine and
 (b) the other $X_1$ must always be hydrogen;
which comprises
 (a) reacting in an inert solvent a compound of formula

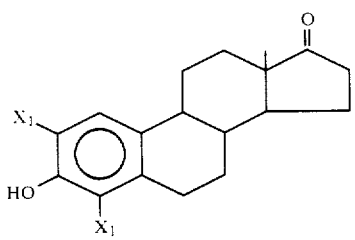

wherein one of $X_1$ is fluorine and the other $X_1$ is hydrogen with a compound selected from the group consisting of formula

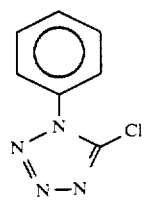

or perfluoroalkylsulfonyl chloride of from one to four carbons, inclusive; and (b) reducing the product of (a) with a reducing agent, such as sodium borohydride and (c) then hydrogenating in the presence of a catalyst to obtain Compound IV.

21. A process for the preparation of a compound having the formula

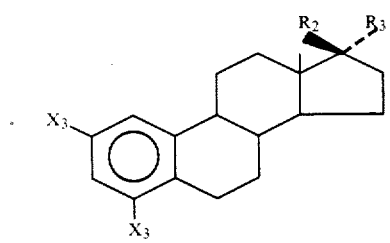

wherein $R_2$ and $R_3$ are different and are
(a) hydrogen, or
(c) hydroxy and
wherein one of $X_3$ is
(a) amino
and the other $X_3$ is
(b) hydrogen
which comprises
(a) reacting in an inert solvent a compound of formula $I_2$
wherein one of $X_2$ is nitro and the other $X_2$ is hydrogen with a compound of formula

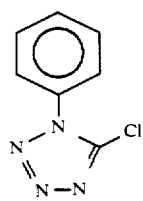

or perfluoroalkylsulfonyl chloride; and (b) reducing the product of (a) with a reducing agent such as sodium borohydride and (c) then hydrogenating in the presence of a catalyst to obtain compound XI above.

22. A process for the preparation of a compound having the formula

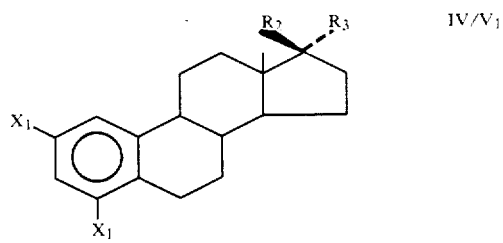

wherein $R_2$ and $R_3$ are
(a) hydrogen,
(b) hydroxy, or
(c) taken together are keto, and with the proviso that both cannot be hydrogen or hydroxy at the same time and wherein one of $X_1$ is
(a) halogen and the other $X_1$ is
(b) hydrogen
which comprises reacting in an inert solvent a compound of formula

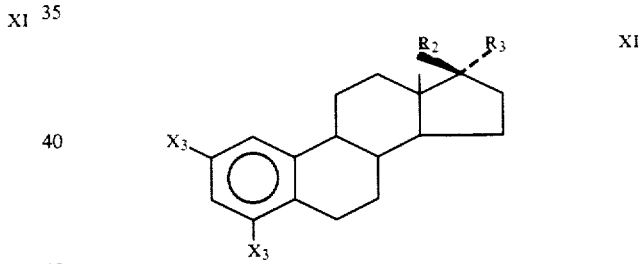

wherein one of $X_3$ is amino and the other is hydrogen and wherein $R_2$ is hydroxy and $R_3$ is hydrogen with a halogenating agent.

23. A process for the preparation of a compound having the formula

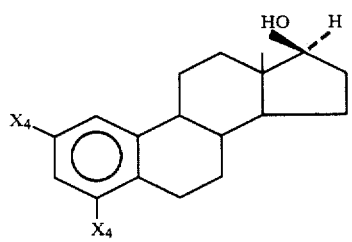

wherein one of $X_4$ is nitro and the other $X_4$ is hydrogen which comprises reacting in an inert solvent a compound of formula

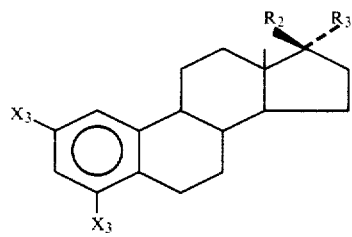

wherein one of $X_3$ is amino and the other is hydrogen wherein $R_2$ is hydroxy and $R_3$ is hydrogen with an oxidizing agent to otain XIII.

24. A process for the preparation of a compound having the formula

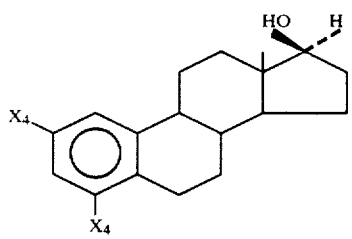

wherein one of $X_4$ is hydroxy and the other $X_4$ is hydrogen which comprises reacting a compound having the formula

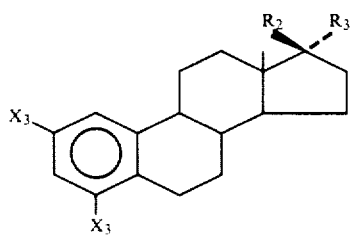

wherein one of $X_3$ is amino and the other is hydrogen and wherein $R_2$ is hydroxy and $R_3$ is hydrogen with sodium nitrite in aqueous mineral acid.

25. A process for preparing a compound having the formula

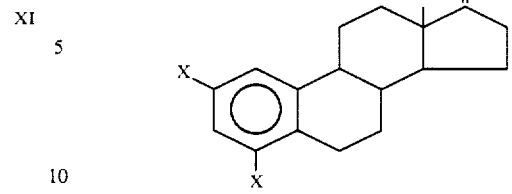

wherein one of X is
 (a) halogen
 (b) amino
 (c) nitro
 (d) hydroxy and the other X is
 (e) hydrogen
which comprises reacting a compound having the formula

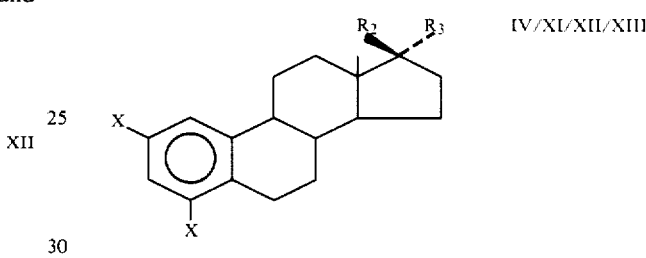

wherein $R_2$ is hydroxy and $R_3$ is hydrogen and wherein one of X is
 (a) halogen
 (b) amino
 (c) nitro
 (d) hydroxy and the other X is
 (e) hydrogen with an oxidizing agent.

26. A compound having the formula

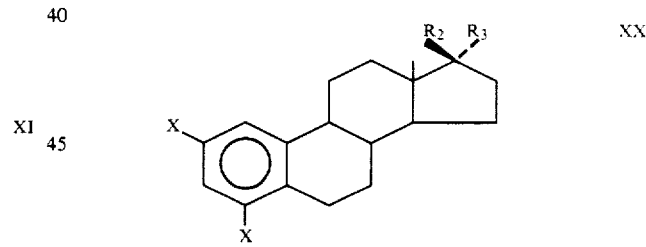

wherein $R_2$ and $R_3$ are the same or different and are
 (a) hydrogen,
 (b) hydroxy, or
 (c) taken together are keto
with the proviso that both cannot be hydrogen at the same time; and wherein one of X is
 (a) halogen,
 (b) nitro,
 (c) amino, or
 (d) hydroxy and
with the proviso that the other X must always by hydrogen.

* * * * *

UNITED STATES PATENT OFFICE
CERTIFICATE OF CORRECTION

Patent No. 4,496,555

Dated 29 January 1985

Inventor(s) S.C. Brooks

It is certified that error appears in the above-identified patent and that said Letters Patent are hereby corrected as shown below:

Column 6, line 60: "Formula $I_2$ is nitro" should read --Formula $I_2$ wherein one of $X_2$ is nitro--.

Column 8 (End of Table 2): "a., b. and c. explanations are missing" should read --a. Incubations were carried out for two hours at 37°C with 400 mg whole porcine uterine tissue (secretory, overectomized pig was injected with 250 mg $E_2$ over a seven day period; then with 25 mg of Pg over a three day period) in 2.5 ml Krebs-Ringer bicarbonate buffer containing $4 \times 10^{-9}$ M $[^3H]$-$E_2$ (sp. act. 100 Ci/mmole). b. Inhibitors were added to experimental incubations at 3 concentrations 10, $10^2$ and $10^3$ times the concentration of $[^3H]$-$E_2$. The tissue was incubated (37°) with the inhibitor for 2 hr prior to the additions of $[^3H]$-$E_2$. c. Following the incubations, the estrogens were extracted from the buffer with ethyl acetate and from the tissue with ethanol. The extracted estrogen sulfates were separated from free estrogens on ITLC (SA) and resolved on ITLC (SG).--

Column 9, lines 5 and 6: "days 21-35" should read --days during the days 21-35--.

Column 10, line 8: "30 of" should read --30 ml of--.

Column 11, line 32: "$O_4$; H," should read $O_4$; C, 65.34; H,--.

Column 11, line 51: "17δ" should read --17β--.

UNITED STATES PATENT OFFICE
CERTIFICATE OF CORRECTION

Patent No. 4,496,555    Dated 29 January 1985

Inventor(s) S.C. Brooks

It is certified that error appears in the above-identified patent and that said Letters Patent are hereby corrected as shown below:

Column 14, line 40: (blank) should read

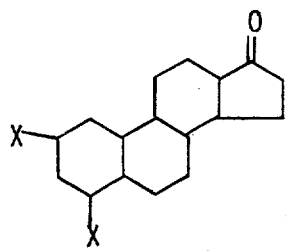

Column 14, line 52: "Example" should read --Example 1--.
Columns 17-18 (after XIII): (blank) should read --Scheme E--.

Signed and Sealed this

Fourteenth Day of October, 1986

[SEAL]

Attest:

DONALD J. QUIGG

Attesting Officer        Commissioner of Patents and Trademarks